US009014427B2

(12) United States Patent
Bear et al.

(10) Patent No.: US 9,014,427 B2
(45) Date of Patent: Apr. 21, 2015

(54) MEDICATION STORAGE DEVICE AND METHOD

(71) Applicant: MedSentry, Inc., Westborough, MA (US)

(72) Inventors: David Bear, Weston, MA (US); Bret Siarkowski, Marlborough, MA (US); Lori Donovan, Shippensburg, PA (US)

(73) Assignee: MedSentry, Inc., Westborough, MA (US)

( * ) Notice: Subject to any disclaimer, the term of this patent is extended or adjusted under 35 U.S.C. 154(b) by 169 days.

(21) Appl. No.: 13/745,175

(22) Filed: Jan. 18, 2013

(65) Prior Publication Data

US 2013/0195326 A1    Aug. 1, 2013

Related U.S. Application Data

(60) Provisional application No. 61/588,795, filed on Jan. 20, 2012, provisional application No. 61/648,304, filed on May 17, 2012.

(51) Int. Cl.
| | |
|---|---|
| G06K 9/00 | (2006.01) |
| A61J 7/00 | (2006.01) |
| A61J 7/04 | (2006.01) |
| G06F 19/00 | (2011.01) |
| A61J 1/03 | (2006.01) |

(52) U.S. Cl.
CPC ........ *A61J 7/0076* (2013.01); *A61J 7/04* (2013.01); *A61J 7/0084* (2013.01); *A61J 7/0481* (2013.01); *A61J 2200/30* (2013.01); *A61J 2200/70* (2013.01); *A61J 2205/30* (2013.01); *A61J 2205/70* (2013.01); *G06F 19/3456* (2013.01); *G06F 19/3462* (2013.01); *A61J 1/03* (2013.01)

(58) Field of Classification Search
USPC ......... 382/100, 103, 110, 128, 181, 190, 195, 382/203, 206; 348/135, 143, 169–172; 705/2; 700/213, 231, 232, 236, 241
See application file for complete search history.

(56) References Cited

U.S. PATENT DOCUMENTS

| | | | | |
|---|---|---|---|---|
| 6,068,156 | A | * | 5/2000 | Liff et al. .......................... 221/7 |
| 7,693,603 | B2 | * | 4/2010 | Higham ........................ 700/242 |
| 7,720,694 | B2 | * | 5/2010 | Potuluri et al. ................... 705/2 |
| 7,930,064 | B2 | * | 4/2011 | Popovich et al. ............. 700/244 |

(Continued)

OTHER PUBLICATIONS

International Search Report for International Patent Application No. PCT/US2013/022177 mailed Mar. 29, 2013 (3 pages).

*Primary Examiner* — Anand Bhatnagar
(74) *Attorney, Agent, or Firm* — Cooley LLP

(57) ABSTRACT

Devices, systems, and methods for monitoring and enhancing patient adherence to a prescription drug regimen are disclosed herein. In some embodiments, a medication storage device includes a plurality of dose containers, each dose container having an interior region configured to contain a medication. The medication storage device also includes an event detection system that includes a plurality of sensors. The plurality of sensors are configured to detect a change in each dose container of the plurality of dose containers. The medication storage device also includes an imaging system. The imaging system includes a plurality of image capture devices configured to capture an image of the interior region of each dose container of the plurality of dose containers. A communications module is configured to send an indication of the change detected by the event detection system and/or an image captured by the imaging device to a remote device.

20 Claims, 9 Drawing Sheets

(56) References Cited

U.S. PATENT DOCUMENTS

| | | | |
|---|---|---|---|
| 7,978,564 B2* | 7/2011 | De La Huerga | 368/10 |
| 8,417,539 B2* | 4/2013 | Chapman et al. | 705/2 |
| 2001/0028308 A1 | 10/2001 | De La Huerga | |
| 2007/0265880 A1* | 11/2007 | Bartfeld et al. | 705/2 |
| 2008/0119958 A1* | 5/2008 | Bear et al. | 700/244 |
| 2008/0306761 A1* | 12/2008 | George et al. | 705/2 |
| 2009/0080735 A1* | 3/2009 | Chapman et al. | 382/128 |
| 2011/0119073 A1 | 5/2011 | Hanina et al. | |

\* cited by examiner

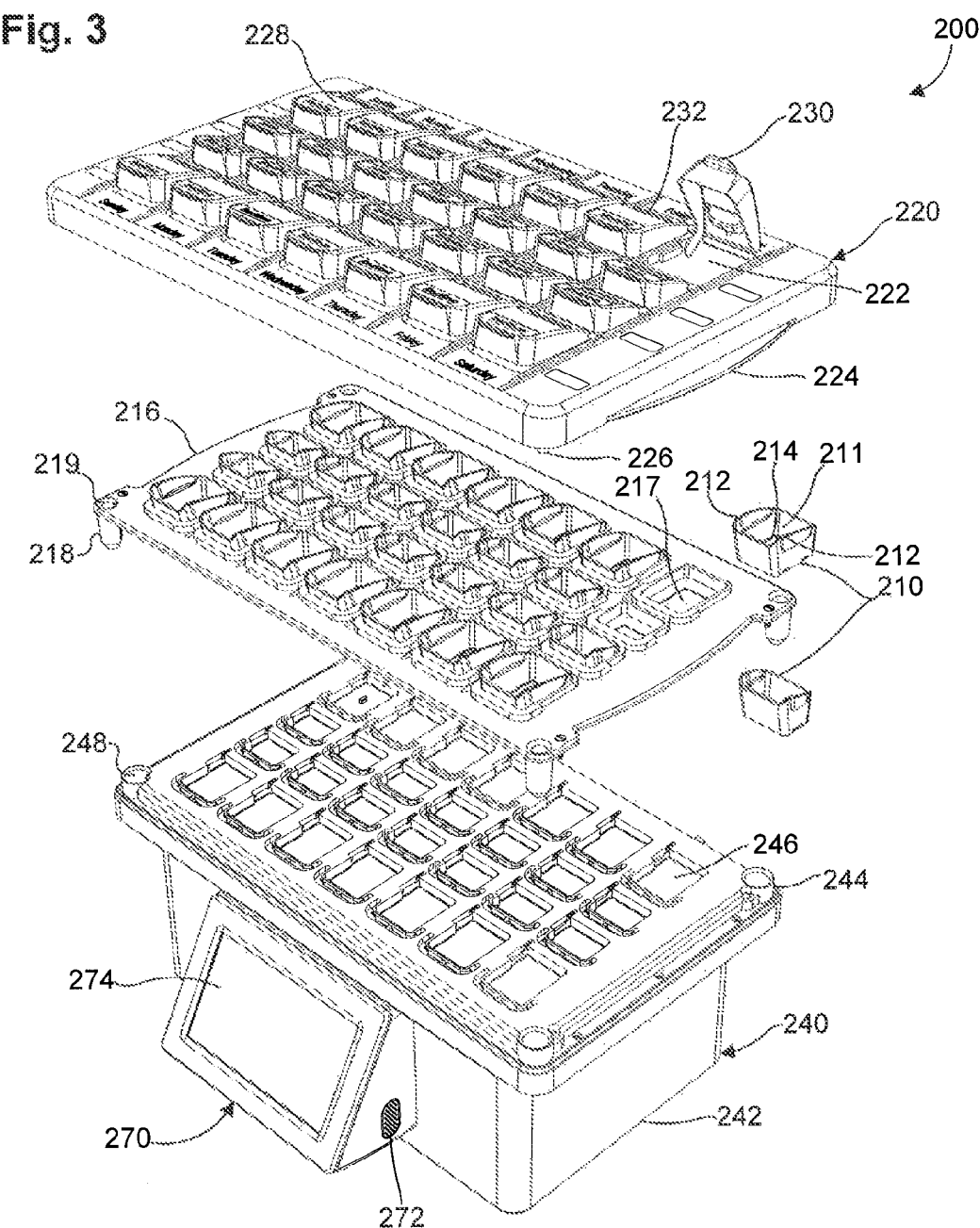

MEDICATION STORAGE DEVICE AND METHOD

CROSS REFERENCE TO RELATED APPLICATIONS

This application claims priority to and the benefit of U.S. Provisional Application No. 61/588,795, filed Jan. 20, 2012, and U.S. Provisional Application No. 61/648,304, filed May 17, 2012, the disclosures of each of which are hereby incorporated by reference in their entirety.

BACKGROUND

Embodiments described herein relate generally to devices, systems and methods for monitoring patient adherence to treatment regimens, and particularly to such a device that enhances patient adherence to a prescription medication regimen.

Adherence is commonly defined as the extent to which a patient complies with a clinician's recommended treatment regimen (e.g., by taking prescribed medications). Medication non-adherence contributes to 125,000 deaths annually in the United States, leads to 10-25% of hospital and nursing home admissions, and costs $300 billion annually in excess medical expenses.

Hospital costs due to patient non-adherence are estimated at $8.5 billion annually. With the recent intensive movement to cost sharing (e.g., Accountable Care Organizations), hospital systems face severe financial penalties for early re-hospitalizations based on medication non-adherence following discharge. Studies show that approximately 50% of the 2 billion prescriptions filled each year are not taken as prescribed. (J. A. Cramer et al., "How Often Is Medication Taken as Prescribed? A Novel Assessment Technique," *Journal of the American Medical Association* (9 Jun. 1989)). Low adherence to prescribed treatments has been shown to undermine treatment benefits. (Sackett D L, Snow J C. The magnitude of adherence and non-adherence. In: Haynes R B, Taylor D W, Sackett D L, eds. *Adherence in Health Care*. Baltimore, Md.: Johns Hopkins University Press; 1979:11-22).

Another area where patient adherence is particularly essential is in drug clinical trials, because non-adherence can lead to erroneous data that can skew the results of the clinical trial. The motivation of clinical trial subjects to adhere to the prescribed drug regimen can be variable leading to a higher rate of non-adherence. Since the cost of a single drug trial is generally in the range of billions of dollars, it is imperative to monitor and ensure adherence of the study subjects to the prescribed regimen.

Several studies have found that although systems and methods of enhancing compliance are available, such systems and methods are labor intensive and complex, thereby complicating dissemination and general usability. Thus, a majority of findings indicate that the full benefit of medications being prescribed is not being achieved due to low adherence levels (Haynes et al. 2002).

While the medication non-adherence problem has been clearly identified, the current monitoring/reminding systems do not provide a comprehensive solution that scales and addresses the multiple challenges to medication adherence. Thus, a need exists for improved and simplified devices, systems, and methods for monitoring and improving patient adherence to treatment regimens.

SUMMARY

Devices, systems, and methods for monitoring and enhancing patient adherence to a prescription drug regimen are disclosed herein. In some embodiments, a medication storage device includes a plurality of dose containers, each dose container having an interior region configured to contain a medication. The medication storage device also includes an event detection system that includes a plurality of sensors. The plurality of sensors are configured to detect a change in each dose container of the plurality of dose containers. The medication storage device also includes an imaging system that includes a plurality of image capture devices configured to capture an image of the interior region of each dose container of the plurality of dose containers. A communication module included in, or operably coupled to, the medication storage device is configured to send an indication of the change detected by the event detection system and/or an image captured by the imaging device to a remote server.

BRIEF DESCRIPTION OF THE DRAWINGS

FIG. 3 is an exploded view of the dose containers and dose container tray included in the medication storage device of FIG. 2.

DETAILED DESCRIPTION

Figure 1:
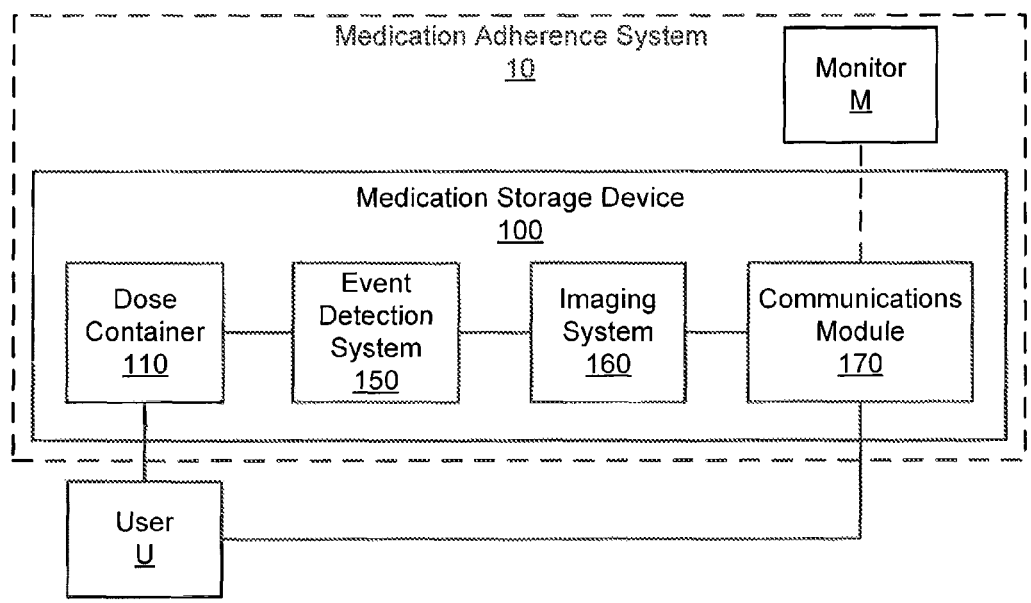
FIG. 1 is a schematic illustration of a medication storage device according to an embodiment.

Devices, systems, and methods for monitoring and enhancing patient adherence to a prescription drug regimen are disclosed herein. In some embodiments, a medication storage device includes a plurality of dose containers, each dose container having an interior region configured to contain a medication. The medication storage device also includes an event detection system that includes a plurality of sensors. The plurality of sensors are configured to detect a change in each dose container of the plurality of dose containers. The medication storage device also includes an imaging system. The imaging system includes a plurality of image capture devices configured to capture an image of the interior region of each dose container of the plurality of dose containers. A communications module included in, or operably coupled to, the medication storage device is configured to send an indication of the change detected by the event detection system and/or an image captured by the imaging device to a remote server.

In some embodiments, a medication storage device includes a plurality of dose containers having an interior region configured to contain a medication, an event detection system including a plurality of sensors configured to detect a change in each of the plurality of dose containers, an imaging system including a plurality of image capturing devices, configured to capture images of the interior region of each of the plurality of dose containers, and a communications module configured to send to a remote server at least one of an indication of the change detected by the event detection system and an image captured by the imaging system. The dose containers can be individually removable from the device or a plurality of dose containers (all of the dose containers or a sub-set of all of the dose containers) can be mounted on one or more removable dose container trays. In some embodiments, the dose containers and/or the dose container tray can have unique identifiers, for example, labels, tags or unique shapes to correspond to at least one day of the week. In some embodiments, the dose containers for a particular dose time (e.g., morning or evening) can be a different shape or size to accommodate a greater number of pills. In other embodiments, the dose containers can have lids that can include unique identifiers such as, for example, labels or tags to indicate the day of the week the medication contained therein is to be taken. After removal, the dose containers can be refilled (e.g., by a pharmacist) and then replaced into the device. In some embodiments, the medication storage device can include security features such as, for example, biometric identifiers (e.g., facial recognition, fingerprints, palm prints, iris/retinal scan and/or voice recognition) to prevent unauthorized individuals from accessing the medication storage device.

The event detection system is operably coupled to the each of the plurality of dose containers and/or the dose container tray, and is configured to detect a change in each of the plurality of dose containers and/or the dose container tray. The plurality of sensors can be configured to detect an event in the medication storage device such as, for example, the opening of a lid of a dose container, closing of the lid, removal/replacement of a dose container, removal/replacement of a dose container tray, and/or other events. The plurality of sensors can be motion sensors, weight sensors, photoelectric sensors, position sensors, pressure sensors or a combination thereof.

The imaging system includes a plurality of image capture devices such as, for example, CCD cameras, configured to capture an image of the interior region of each dose container of the plurality of dose containers. The plurality of image capture devices can be fixed (i.e., stationary) cameras configured to capture an image of the interior region of single dose container or a plurality of dose containers such that a combination of the plurality of images taken by the imaging system shows the interior region of all of the dose containers. The image capture devices can be configured to capture an image at a fixed interval (e.g., once every second or every minute) or when an event is detected by the event detection system. For example, one of the plurality of image capture devices can be configured to capture an image immediately upon the event detection system sensing the opening of a lid of one of the plurality of dose containers. The same image capture device can also be configured to capture an image of that same dose container when the event detection system senses the closing of the lid. In some embodiments, the image capture device can be configured to capture additional images at predetermined intervals between the opening and closing of the lid. In some embodiments, the imaging system can be configured to capture an image or video of the individual that interacts with the medication storage device. For example, the imaging system can be configured to capture images or video based on a detected event (e.g., motion or sound) to record who adds or removes medication from the medication storage device.

The communications module can be configured to communicate with a remote server, for example, a central computer and/or a call center. The communications module can send an indication that an event has occurred, for example, a dose container lid was opened, and/or to send an image captured by the imaging system. The communications module can also be configured to receive communications from the server and/or to send alerts to the user, for example, improper drug container opened, adjust dosage, get medication refill, etc. The communications module can also be configured to receive home health monitored data (e.g., weight, blood pressure, EKG, oxygen saturation, actigraphy measures, measures of exercise (steps taken), pulmonary function, water retention, blood glucose, temperature, etc.) via wired or wireless protocols (e.g., Bluetooth®, low power Bluetooth®, ZigBee®, or others).

In some embodiments, the medication storage device can be used as part of a system or method of monitoring patient adherence to a treatment regimen. The method can include notifying a patient that it is time to take a prescribed medication, determining if the patient has opened the correct dose container from a plurality of dose containers in the medication storage device, capturing a first image of the dose container when the patient opens the dose container, capturing a second image of the dose container when the patient closes the dose container, comparing the first image and the second image to determine which medication has been removed from the dose container, determining whether the patient has removed the correct medication by comparing the prescribed medication to the removed medication, and alerting the patient, a care giver, a family member, a call center, a pharmacy, or a doctor if an incorrect medication has been removed from the dose container or even if an incorrect dose container has been opened. The notifications and alerts can include visual, audible and/or tactile indications to encourage adherence or warn of errors.

In some embodiments, the medication storage device can be used to ensure that the dose containers are accurately filled with medication. The method can include loading at least one medication into each dose container of a plurality of dose containers in the medication storage device based on prescription data for an individual patient, capturing one or more images of the plurality of dose containers, analyzing the one or more captured images to determine which medication has been loaded into each dose container of the plurality of dose containers, comparing the medication loaded into each dose container of the plurality of dose containers with the prescription data, and alerting the patient, a care giver, a family member, a call center, a pharmacy, or a doctor if an incorrect medication has been loaded into the medication storage device. A computer vision system can be used to analyze the one or more captured images to determine which medication has been loaded into each dose container of the plurality of dose containers.

In some embodiments, the medication storage device can be used as part of a system or method of preventing deviations from a treatment regimen. The method can include determining if a patient has opened an incorrect dose container from a plurality of dose containers in the medication storage device, capturing a first image of the incorrect dose container when the patient opens the incorrect dose container, alerting the patient, a care giver, a family member, a call center, a pharmacy, or a doctor that the incorrect dose container was opened, capturing a second image of the incorrect dose container when the patient closes the incorrect dose container, comparing the first image and the second image to determine if medication has been removed from the incorrect dose container, and alerting the patient, care giver, family member, call center, pharmacy, or doctor if an incorrect medication has been removed. An individual at a staffed call center or computer vision system can be used to determine which medication has been removed from the dose container.

Devices, systems, and methods according to embodiments described herein can be configured for monitoring and enhancing patient adherence to a prescription drug regimen. For example, the medication storage device described herein includes an event detection system that is operably coupled to an imaging system. The event detection system not only records an event that has taken place in a dose container, but it also serves as a trigger for the imaging system to capture a high definition image of the medications in one dose container or a plurality of dose containers. Said another way, the detection of an "event" at a dose container activates the imaging system and/or otherwise causes the imaging system to capture an image as opposed to continuous image capturing or image capturing at predetermined time intervals. Having the imaging system configured to capture images on an as needed basis (e.g., after events are detected) provides increased battery life, reduces data storage and processing requirements, improved data processing speeds. Event related monitoring can be restricted, for example, to a single dose cup or bin, reducing monitoring demands and cost at the call center. The images captured contemporaneous with a detected event also provide the most accurate information on the status of a dose container (e.g., dose container removed/replaced, dose container tray removed/replaced, and/or dose removed/filled).

The medication storage device can also be configured to compare captured images with reference images of the prescribed medication such as, for example, images pre-stored by an authorized medication dispenser (e.g., pharmacy) and/or obtained from a reference database such as that supplied by Thomson Reuters or the National Institutes of Health. Thus, the medication storage device can determine if the correct dose was loaded into the dose containers by the dose dispenser. Similarly, the medication storage device can also be configured to determine if the correct dose has been withdrawn from the dose container by comparing captured images with reference images to ensure that the patient is adhering to the prescribed medication regimen. The combination of data that includes events recorded by the event detection system and images captured by the imaging system provide comprehensive information on patient adherence to a prescribed medication regimen as well as patient history, which can be very beneficial to ensure patient well-being. For example, this detailed information can be used to prevent overdose and/or adverse drug interactions (e.g., taking a prescription drug with a forbidden "only as needed medication"). The data can also be used to ensure strict patient adherence to the prescribed regimen in cases where any deviations can be detrimental to the patient, society (e.g., anti-depressant or an anti-psychotic medication) and/or a scientific study (e.g., clinical trials).

As described herein, the imaging system includes a plurality of stationary cameras instead of positionable or movable cameras. Stationary cameras obviate the need for complex mechanical instrumentation such as linear motors, slide rails, and/or position sensors in the imaging system that can require periodic maintenance and/or fail. In other words, the plurality of stationary cameras provide redundancy in the system such that if one camera fails or otherwise cannot capture a particular image, other cameras in the imaging system can provide back-up so the system can still operate. For example, in some embodiments, two, three, or even more cameras in the imaging system can be capable of capturing images of any one of the dose containers so failure of one camera does not impact operation of the system. The "back-up" cameras can also be used to capture images from different angles for use in image comparison as described herein. Furthermore, since there are no moving parts, the device is quieter and data acquisition is faster (e.g., substantially simultaneous to a detected event).

FIG. 1 is a schematic block diagram of a medication adherence system 10 that includes a medication storage device 100. The medication storage device 100 includes a plurality of dose containers 110, an event detection system 150, an imaging system 160, and a communications module 170. The medication storage device 100 can contain medication to be taken by a user U (e.g., a patient, a clinical trial subject, etc.) and the communications module 170 can be configured to communicate information to the user U, and/or can be configured to communicate with a monitor M (e.g., an on-site computer, a remote server, a smart phone, a family member, a care giver, a call center, a pharmacy, and/or a doctor). In some embodiments, the communications module 170 can be configured to allow two-way communication between the user U and the monitor M. As used herein, the term "medication" can include medication in any form such as, for example, pills, parenterals, salves, creams, powders, ointments, capsules, injectable medications, drops, vitamins, suppositories, etc.

The dose containers 110 of the medication storage device 100 can be any suitable receptacle suitable for housing or containing medication. For example, each of the plurality of dose containers 110 can define an interior region configured to contain a single medication or a plurality of medications. In some embodiments, the dose containers 110 can be removable from the medication storage device 100. After removal, the dose containers 110 can be disposed of or refilled (e.g., by a pharmacist) and replaced into the medication storage device 100. In some embodiments, the dose containers 110 can be individually removable from the medication storage device 100 and/or a plurality of dose containers 110 (all of the dose containers or a sub-set of all of the dose containers) can be mounted on, or attached to, one or more removable dose container trays (not shown) and the trays can be removable from the medication storage device 100.

In some embodiments, the dose containers 110 can be formed from a material that is lightweight and rigid such as, for example, plastics. The dose containers 110 can be custom manufactured plastic cups that have rounded edges to prevent medication from sticking to the bottom of the cup and allow easy removal of medication by the user U. One side of the dose containers 110 can be rounded to allow medications to be easily poured into the hand or individually removed. In some embodiments, the dose containers 110 can include at least one transparent portion, for example, a transparent base, such that the contents of the interior region of each dose container 110 can be "viewed" by the imaging system 160 as described in further detail below. In some embodiments, at least a portion of the dose containers 110 can have a neutral color (e.g. white or gray) for white balancing of the imaging system 160. In some embodiments, at least a portion of each dose container 110 can be partially transparent and/or translucent to allow lighting of the interior region of the dose containers 110 by, for example, a dedicated light source (e.g., one or more LEDs) or ambient light, and/or to allow recording of an event in each dose container 110 by the event detection system 150 as described in further detail below.

In some embodiments, the dose containers 110 can be configured to hold a plurality of the same medication, for example, three 200 mg tablets for a 600 mg dose, or a combination of various medications, for example, a diabetes managing tablet, a cholesterol reducing tablet, an arthritis capsule, a blood pressure soft gel and/or other medication as prescribed. In some embodiments, the dose containers 110 can be approximately 1½ inches in diameter and can hold up to 12 individual medications while having minimal overlap of pills. In other embodiments, where the medication is too large to fit into a dose container 110, for example, an inhaler, a parenteral, an injectable, a patch and/or a "lollipop" like medication stick, a medication reminder marker can be placed in the dose container 110 in lieu of the medication. The medication reminder marker can be a label, a coin shaped plastic chip, and/or a paper slip. In some embodiments, the medication reminder marker can have a color and label that matches the color or label on a prescribed medication.

In some embodiments, the dose containers 110 and/or the dose container tray can have unique identifiers, for example, labels, tags or unique shapes to correspond to at least one day of the week. In other embodiments, the dose containers 110 can have lids that can include unique identifiers such as, for example, labels or tags to indicate the day of the week on which the medication is to be taken.

In some embodiments, the dose containers 110 can be arranged in an array to match a user's U treatment regimen. For example, the dose containers 110 can be arranged in a "number of doses per day+1" by "day of the week" (e.g., N+1×7) array. Said another way, the dose containers 110 can be arranged in a 2 dose/day×7 days, 3 dose/day×7 days, or 4 dose/day×7 days dosing regimen with optionally, an extra row (+1 row) for prn (only when needed) medication. In some embodiments, the prn dose containers 110 allow the medication adherence system 10 to monitor and track the "only when needed" medication, for example, pain killers, anti nausea drugs, cough and cold medication, etc., and provide alerts if the prn medication is taken prematurely or too many prn medications are taken. This feature of being able to monitor particular types of medication can be useful in preventing dangerous drug interactions and/or overdosing.

The event detection system 150 includes a plurality of sensors configured to detect a change in each dose container of the plurality of dose containers. In some embodiments, each sensor of the plurality of sensors is associated with an individual dose container 110. In some embodiments, multiple sensors are associated with each individual dose container 110. In some embodiments, a sensor is associated with multiple dose containers 110 (e.g., a sub-set of the plurality of dose containers). The sensors can be position sensors, photoelectric sensors, pressure sensors, weight sensors and/or motion sensors. In some embodiments, each of the plurality of sensors can be a solid state sensor that is relatively small, has low power requirements, is inexpensive, quiet and durable. The event detection system 150 can be configured to detect an event occurring in each dose container 110, for example to detect dose container removal, dose container replacement, dose container present, dose container lid opened, dose container lid closed, dose container tray removal, dose container tray replacement, device connected to power supply, and/or device using backup battery, etc. In some embodiments, the event detection system 150 can trigger an alert, which is delivered by the communications module 170 to the user U and/or the monitor M. As described above, the event detection system 150 can cause the imaging system 160 to capture an image of a single or a plurality of the dose containers 110.

In some embodiments, the event detection system 150 can include a lighting module (not shown) for illuminating the dose containers 110. For example, the lighting module can include a plurality of light sources such as LEDs, configured to illuminate the plurality of dose containers 110 for better imaging of the dose containers 110 by the imaging system 160 or for improved visualization by the user U. The lighting module can also be configured to perform notification functions such as, for example, illuminating the dose container 110 that correlates with a dose to be taken at a particular time, blinking if the dose is not taken by the prescribed time, blinking if wrong dose container is open, and/or blinking a plurality of LEDs to notify the user U of a critical event.

The imaging system 160, is configured to capture an image of the medications contained in the interior region of each of the dose containers 110, for example to ensure that the proper prescription was filled, proper dose was removed, and/or to keep periodic track of the patient's adherence to the prescribed medication regimen. The imaging system 160 can include a plurality of image capture devices. In some embodiments, the number of image capture devices is equal to the number of dose containers 110 such that, for example, each image capture device is configured to capture an image of a single dose container 110. In other embodiments, the number of image capture devices is substantially less than the number of dose containers 110 such that a combination of images captured by each of the plurality of image capture devices can show an image of the doses disposed in the interior region of all the dose containers 110. In some embodiments, the image capture devices can be arranged in an array and can be fixed in the housing (not shown) of the medication storage device 100. In some embodiments, the array of cameras can be configured such that two or more cameras in the array are capable of capturing images of any one of the dose containers 110 so failure of one camera does not impact operation of the system. The "back-up" camera or cameras can also be used to capture images from different angles for use in image comparison as described herein. In some embodiments, the image capture devices can also be disposed on and/or coupled to the lids of the dose containers 110, for example, to enable viewing of the medications in the dose containers 110 from above. In some embodiments, each of the plurality of image capture devices can be a solid state device, for example, a CCD camera, and can further be disposed in fixed positions (i.e. stationary). Solid state devices are advantageous in their durability, size, low power requirements, reduction in assembly cost and silent operation. As described above, the use of stationary image capture devices eliminates mechanical parts, thereby reducing mechanical failure and maintenance costs, and reducing noise of operation. The imaging system 160 can further include focusing and/or magnification optics, for example, lenses, mirrors, image processing hardware and/or software, lighting, polarizing filters and/or white balancing to ensure accurate color rendition.

The imaging system 160 can be configured to capture images of the interior region of each of the dose containers 110 to identify the medication disposed therein. For example, the imaging system 106 can capture an image of multiple drugs, e.g. 2, 3, 4, up to 12 drugs, or even a higher number in each dose container 110 and with a sufficiently high resolution to resolve individual representative features on the drugs (e.g., shape, size, color, inscriptions, scoring, beveling, embossment, debossment, and/or division of a tablet (half or quarter)). The images can be colored or black and white. The images can be digital and stored in various forms locally on the medication storage device 100 or can be transmitted via, for example, the communications module 170, to a monitor M (e.g., a computer at the user's U home, a smart phone such as an Android or iPhone, a care giver, a family member, a doctor, a pharmacy or an authorized call center) where the images can be compared to a reference image database to ensure that the correct prescription is filled. The images can also be used to monitor patient adherence to the drug regimen, for example, correct dose container 110 opened, correct dose removed and/or to notify patient of any changes or alerts regarding the prescribed dose, for example, possible drug interactions, dose changes, dose containers almost empty, etc. In some embodiments, the medication storage device 100 can include a vibrating mechanism operable to selectively vibrate one or more of the dose containers 110 to reposition the medications in the dose containers 110, for example, to improve image capture of individual pills in the dose containers 110 by the imaging system 160.

The communications module 170 is configured to communicate data such as, for example, the occurrence of an event, an image captured by the imaging system 160, and/or other information from the medication storage device 100 to the user U, from the medication storage device 110 to the monitor M, or two-way communication between the user U and the monitor M. In some embodiments, the communications module can include speakers, a microphone, a keyboard, a display (e.g., LCD, touch screen, etc) and/or a vibrating mechanism for tactile alerts. In some embodiments, the communications module 170 can include conventional electronics for data communication and can use a standard protocol, for example, Wi-Fi, Bluetooth®, low powered Bluetooth®, Zigbee®, USB, RJ45 connection via DSL, and/or a telephone line for connection and data communication. In some embodiments, the communications module 170 can also include data storage capabilities, for example, to store event data, image data, reference image database, patient prescription information and/or other patient health monitoring data.

In some embodiments, the communications module 170 can also include a computing module that includes a processor and memory configured to process images and/or execute computer vision algorithms (e.g., mutual information, linear discriminant analysis, quadratic discriminant analysis, Naives Bayes classifier, neural networks, Gaussian process regression, K-means clustering, etc.) to compare images of the dose containers 110 with reference images. In some embodiments, the communications module 170 can also include a notification system configured to provide audio, visual, and/or tactile alerts to a patient or communicate with patient as described in detail below. In some embodiments, the communications module 170 can be integrated into the medication storage device 100. In some embodiments, the communications module 170 can be a separate device, for example, a smart phone (Android, iPhone), a tablet, a local computer a remote computer, and/or server, etc., that can communicate with the medication storage device 100 via a network, which may be any type of network (e.g., a local area network or LAN, a wide area network or WAN, a virtual network, a telecommunications network, and/or the internet) implemented as a wired network and/or a wireless network. Any or all communications may be secured (e.g., encrypted) or unsecured.

In some embodiments, the communications module 170 can be activated on demand, for example, by the user U through a communication interface (not shown) or remotely by an automated system, for example, by a smart phone application and/or the monitor M. In some embodiments, the communications module 170 can be configured to periodically reestablish connection with the monitor M for real-time monitoring of the medication storage device 100. This can be useful, for example, in an event where the medication storage device 100 is unplugged or loses power.

In some embodiments, the communications module 170 can be configured to receive home health monitored data such as, for example, weight, blood pressure, EKG, oxygen saturation, actigraphy, measures of exercise (e.g., steps taken), pulmonary function, water retention, blood glucose, temperature and/or other medically relevant information that can be collected at the user's U home. The user U can enter this data manually into the communications module 170 through the communication interface, through a voice recognition capability of the communications module 170, or the communications module 170 can be configured to wirelessly interface and collect information from other home health monitoring devices/equipment. In some embodiments, the health monitoring data can be correlated with the dose compliance data collected by the medication storage device 100. This combined/correlated data can be used to determine the efficacy of the prescribed drug regimen, side effects, changes to prescribed dosage and/or overall patient health progression.

As described herein, the communications module 170 can include a notification system configured to provide an alert when it is time for the patient (e.g., User U) a prescribed medication. For example, the notification system can be configured to turn on an LED of the lighting module to illuminate the correct dose container 110. In some embodiments, the vibrating mechanism can be configured to vibrate the correct dose container 110. In some embodiments, the notification system can be configured to display a message such as, for example, "It's time for your evening dose Mr. Jones." In some embodiments, the notification system can be configured to produce an audible message and/or a signal such as, for example, a beep or alarm. In some embodiments, the notification system can be configured to provide a reinforcement message (audible or visual) such as, for example, "well done Mr. Jones" if the correct dose container 110 is accessed at the prescribed time.

In some embodiments, the communications module 170 can be configured to provide reminders and/or warning if a dose container 110 is not accessed at the prescribed time or if the wrong dose container is accessed. For example, the communications module 170 can be configured to communicate an escalating audible, visual or tactile signal to the user U after predetermined time thresholds to remind the user U to take their medication. After a predetermined time has elapsed and/or a predetermined number of reminders have been communicated to the user U without the correct medication being taken, the communications module 170 can be configured to communicate an alert to the monitor M.

In some embodiments, the communications module 170 can be configured to recognize an erroneous event, for example, wrong dose container 110 being opened, and communicate an audible, visual or tactile signal to the user U. If no remedial action is taken after a predetermined period of time, the communications module 170 can be configured to communicate an alert to the monitor M. In some embodiments, the communications module 170 can be configured to detect a critical event, for example, too many dose containers 110 being opened, and communicate an alert to the user U, and at the same time or after a predetermined time, to communication an alert to the monitor M and/or emergency personnel (e.g., call 911). In some embodiments, the communications module 170 can be configured to automatically call the patient's pharmacy when it is time for a refill.

In some embodiments, the notification system can be configurable by the user U. For example, the user U can use the communications module 170 interface (e.g., keyboard, touch screen, etc.) to input preferences such as alarm tones, clock time, activate/deactivate alarms (with permission from monitor M), view dosage information, set alarms, lighting preferences, display messages, voice, sound, email/message preferences, and/or message frequency. Furthermore, the user U can also deactivate the notification system, for example, if the patient is travelling, hospitalized, sleeping, or discontinues use for an extended period of time. In other embodiments, the notification system is preset based on prescription data. In some embodiments, the notification system can be configured to notify other scheduled activities of the user 110, e.g., health reminders such as "check your weight", "check your blood pressure", "time to refill your prescription" and/or social reminders such as "today is bingo day". In some embodiments, a doctor can communicate information through a telemedicine visit to the user U through the communications module 170 to advise user U of any changes to their treatment regimen.

In some embodiments, the communications module 170 can include voice recognition (VR) capabilities for receiving prescription updates from an authorized medication prescriber, e.g., doctor, and automatically update the user's U prescription regimen in the medication storage device 100. For example, the patient can take the medication storage device 110 or a removable communications module 170 (e.g., smart phone) to a doctor appointment where the communications module 170 can read and/or display the current user U prescription to the doctor. The doctor can use the voice recognition capability of the communications module 170 to record the updated medication regimen to the medication storage device 100. In some embodiments, the vocabulary allowed for recording deletion can be highly limited, for example, less than 10 items. In some embodiments, the vocabulary allowed for addition of medications can be less restrictive, for example, a vocabulary of less than 1,500 items. The syntax of prescribing can be fixed and rigid, e.g. "Clonazepam 1 mg po every 12 hours". The voice recognition can be capable of capturing dosing even if titration is involved, e.g., "Clonazepam 1 mg po every 12 hours for 5 days; then clonazepam 0.5 mg po every 12 hours." The updated prescription medication list can also be communicated to the monitor M, to all authorized physicians, and/or to authorized medication dispensers, e.g. pharmacy, doctor, clinical trial manager. Any adverse effects or interactions can therefore be identified in a timely manner and rectified.

The monitor M can monitor and ensure patient adherence to the prescribed treatment and/or prescription regimen. In some embodiments, the monitor M can be integrated with the medication storage device 100. For example, the computing module of the communication module 170 can be configured to serve as the monitor M as described above and no external monitoring is performed. In some embodiments, the monitor M can be an external entity, for example, a family member, a care giver, a nurse, a pharmacy, a doctor, a clinical trial manager, and/or a call center. In some embodiments, the monitor M can be a computer configured to automatically monitor patient adherence to a treatment regimen. For example, if the user U takes the prescribed dosage at the correct time, the event detection system 150 can record an event and the imaging system 160 can capture an image of the dose container 110. The communications module 170 can further communicate data of the event and/or the image of the dose container 110 to the monitor M, where data is time stamped and recorded but no action is taken. If the user U fails to take prescribed dosage even after the time threshold set for audible or visual notifications on the notification system, the computing system can convey an alert to the monitor M. The monitor M can then contact the user U, e.g., via email, text message, phone call, audio/visual interface of the notification system, and/or personal visit to correct the action. The same protocol can be followed in case of an event where a wrong dose container 110 is opened and/or removed. In case of a critical event, for example, too many dose containers opened simultaneously, an immediate alert can be sent to the user U and the monitor M. The monitor M can respond by contacting the user U, e.g. by audio/visual/tactile notification on the medication storage device 100, phone call, text message, and/or personal visit, and if no response is received, call the emergency personnel.

In some embodiments, the monitor M can ensure that the medication storage device 100 is accurately filled with medication. For example, drugs can be loaded into the dose containers 110 and the imaging system 160 can capture an image or images of the medications in the each of the dose containers 110. The image data can be communicated by the communications module 170 to the monitor M, where the image data can be compared with a reference database as described herein. If the correct medications and dosages were loaded into the plurality of dose containers 110, the data can be time stamped and stored. If an inaccuracy is determined, the monitor M can alert the patient, a care giver, a family member, a pharmacy, a doctor, and/or a clinical trial manager. Once the inaccuracy is rectified and the proper dosage is filled, the method can be repeated again until accuracy is achieved.

In further embodiments, the monitor M can also prevent deviations from a treatment regimen. For example, at the prescribed time, the user U can access the dose container 110 to extract medication. The event detection system 150 can record an event and the imaging system 160 can take an image of the dose container 110. The event and image data can further be communicated to the communications module 170 and/or monitor M, where the image of the medications in dose container 110 can be compared to a database of the prescribed medication. If the correct dose was removed, the data is time stamped, stored and no further action is taken. If there is a deviation in dose removed, for example, if the user U was prescribed 600 mg of a medication but only 300 mg of the medication (half tablet) was withdrawn from the dose container 110, the monitor M can send an alert to the user 110 and notify him of the deviation. If the deviation is not corrected, further alerts can be sent to a care giver, a loved one, a doctor, and/or a clinical trial manager.

Having described above various general principles, several exemplary embodiments of these concepts are now described. These embodiments are only examples, and many other configurations of a medication storage device, systems and/or methods for monitoring and ensuring patients adherence to a prescribed medication regimen, are contemplated.

Figure 2:
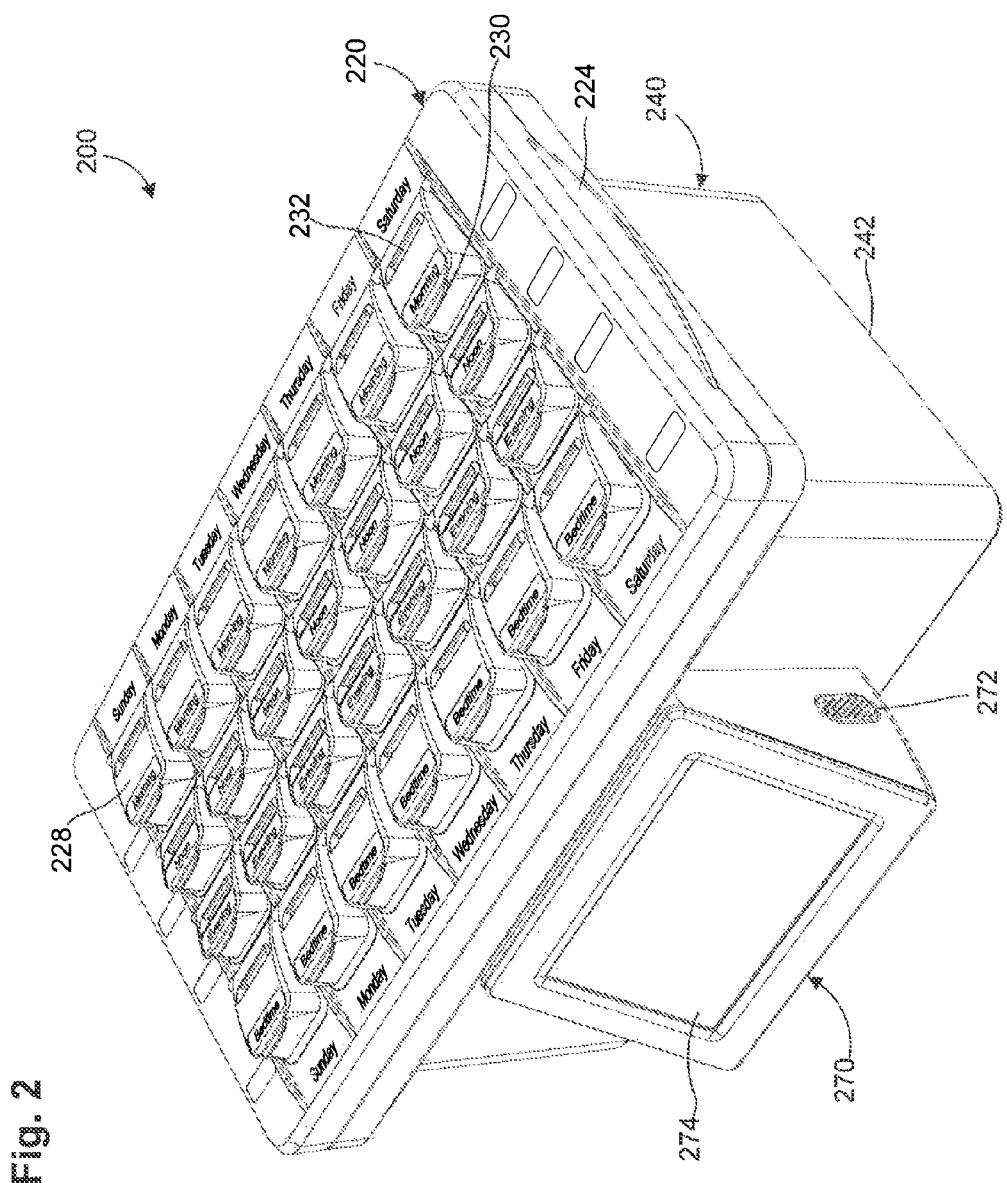
FIG. 2 is a perspective view of a medication storage device according to an embodiment.

Referring now to FIGS. 2 and 3, a medication storage device 200 includes a plurality of dose containers 210, a dose container tray 216 (also referred to as a "tray" herein), a cover 220 and a base 240. As described herein, the dose containers 210, the tray 216, the cover 220 and the base 240 can be removably coupleable to each other for service and maintenance, or to provide easy removal of the dose containers 210 for filling a prescribed medication regimen.

As shown in FIG. 3, the dose containers 210 are receptacles that define an interior region 211 suitable for housing or containing a plurality of medications. In some embodiments, the dose containers 210 can be formed from a light-weight and rigid material such as, for example, plastics. For example, the dose containers 210 can be custom manufactured plastic cups. In some embodiments, the dose containers 210 can be rectangular in shape. In some embodiments, the dose container 210 can be square, circular, oval, rectangular or any other suitable shape. In some embodiments, the dose containers 210 can be approximately 1½ inches in cross-section (or diameter) and can hold up to 12 or more individual medications while having minimal overlap of pills. In some embodiments, the dose containers 210 can have rounded edges, for example, to prevent medications from sticking to the bottom of the dose container 210 and allow easy removal of medication by a patient. In some embodiments, the sides of the dose containers 210 can be rounded, for example to allow medications to be easily poured into the hand or individually removed. In some embodiments, the dose containers 210 can also include protrusions, for example, tabs, notches, detents, overhang and/or contoured walls to allow easy removal of the dose containers 210 from tray 216 as described below.

In some embodiments, the dose containers 210 can include a base 212 that is at least partially transparent to allow "viewing" of the interior region 211, for example, by an imaging system (not shown in FIGS. 2 and 3). The base 212 can be an integral part of the dose container 210, for example, formed in a single manufacturing process (e.g., plastic molding) or it can be a separate member that is coupled to the bottom of the dose container 210. In some embodiments, at least a portion of each dose container 210 can have a neutral color (e.g. white or gray) for white balancing of the imaging system. In some embodiments, a second portion of the dose container 210 can be partially transparent and/or translucent to allow lighting of the interior region 211 of the dose container 210, for example, by ambient light, a dedicated light source (e.g. one or more LEDs) and/or to allow recording of an event in each dose container 210, for example, by sensors of an event detection system (not shown in FIGS. 2 and 3).

In some embodiments, the dose containers 210 can be arranged in an array to match a patient's medication regimen. For example, the dose containers can be arranged in a "number of doses per day" by "days of the week" (e.g. N×7) array. For example, the array can be 4 doses per day e.g. morning, noon, evening, bedtime, for 7 days a week. In some embodiments, an extra row for prn medication can be included (+1 row). For example, the dose containers 210 can be arranged in an "N+1×7" array. In some embodiments, the dose containers 210 can have unique identifiers, for example, labels, tags or unique shapes to correspond to at least one day of the week. In some embodiments, the plurality of dose containers 210 can be coupled to each other, for example, the dose containers 210 containing medication for all doses of a single day of a week, dose for a week, dose for a month, and/or dose for each dosage time of the day/week can be coupled together.

The tray 216 can be formed from a light-weight and rigid material, for example plastic, and can include individual apertures 217 shaped and sized to receive at least one dose container 210 from the plurality of dose containers 210. The tray can further be shaped and sized to be removably coupleable to the base 240. In some embodiments, the tray 216 can include alignment features 218, e.g. pins, notches, detents, have a trapezoidal shape, have selected edges chamfered or filleted, tabs, labels, direction arrows an/or markings to ensure that the tray can be disposed, only in a certain orientation on the base 240. Said another way, the tray 216 can be configured so that there is only one way for the user to insert the tray 216 into the base 240. In some embodiments, the tray 216 can further include recesses 219 configured to provide alignment markers for receiving the cover 220 of the medication storage device 200, as described below.

In some embodiments, the tray 216 has a matrix of individual apertures 217 that can hold a predetermined number of dose containers 210 for a predetermined number of days. The tray 216 can be configurable in accordance with patient dosage, for example 2×, 3× or 4× dose per day which allows for flexibility for a broad range of patient schedules. In some embodiments, the apertures 217 in the tray 216 can be keyed. For example, an aperture 217 corresponding to Monday can be square, Tuesday can be round, Wednesday can be oval, and so on. The dose containers 210 can be shaped and sized accordingly to correspond to a particular aperture 217 on the tray 216, for example, to make sure that the correct dose container 210 is disposed in the appropriate aperture 217 of the tray 216. In some embodiments, the dose containers 210 can be reversibly coupleable to the tray 216. In some embodiments, the dose containers 210 can be permanently coupled to the tray 216 such that the complete dosage for the entire medication regimen (e.g., for the week and/or month) are filled in the dose containers 210 in the tray 216, which is then delivered to the patient. In some embodiments, the tray 216 can also include, for example, labels, bar codes, and/or RFID tags for tracking purposes or to inform the patient which day/week/month medication to load. This can be advantageous, for example, to allow automated filling of a complete prescription regimen of a patient by a pharmacy, doctor, clinical trial manager or any other authorized medication dispenser.

The cover 220 can be formed from a light-weight and rigid material, for example, plastic, and can be configured to be removably coupleable to the base 240 of the medication storage device 200 such that, for example, the cover 220 and the base 240 define an interior region for at least partially housing the dose containers 210 and the tray 216. In some embodiments, the cover 220 can include openings 222 sized and shaped for receiving at least a portion of the dose containers 210. The cover 220 can include a tab 224 for easy removal of the cover from the base 240. In some embodiments, the cover 220 can also include pins 226 that can be configured to serve as alignment features to mate with recesses 219 on the tray 216 to allow easy coupling of the cover 220 to the base 240, and in the proper orientation. In some embodiments, the cover can include snap-fit mechanisms, for example, notches, grooves, detents and/or any other suitable coupling mechanism for reversible coupling to base 240. In some embodiments, a locking mechanism (e.g., spring-loaded latches) can be included on one or multiple sides of the cover 220 to prevent access to the dose container 210 or tray 216 by unauthorized people, for example, children. In some embodiments, the cover 220 can be permanently coupled to the base 240. For example, the cover 220 can be mounted on pivots, swivel mounts, hinged, or tethered to the base 240 such that the cover can rotate from a first, position, wherein the cover 220 is open and the dose containers 210 and/or tray 216 can be removed/replaced, to a second position, wherein cover 220 is closed and the dose containers 210 and/or tray 216 cannot be removed/replaced.

In some embodiments, the cover 220 can include a plurality of lids 228 configured such that when the cover 220 is coupled to the base 240, each of the lids 228 align with a corresponding dose containers 210. In some embodiments, the lids 228 can be coupled to the dose containers 210 and not included in the cover 220. In some embodiments, when the lids 228 are included in the cover 220, the dose containers 210 can have seals such as, for example, decals, stickers, metal foil, paper sheet, or a temporary plastic lid that can be removed before disposing dose containers 210 in the tray 216, after disposing the dose containers 210 in the tray 216, or before coupling the cover 220 to the base portion 240. The lids 228 can be formed from a similar material as the dose containers 210. In some embodiments, the lids 228 can be pivotally mounted on hinges, pivots, slots, notches or a combination thereof on the cover 220 such that it can rotate about a first position wherein the dose containers 210 are closed, to a second position wherein the dose containers 210 are open and medication disposed therein is accessible by the patient. In some embodiments, the lids 228 can be tethered to the cover 220, for example, with a thin piece of plastic, silicone rubber, a metal strip and/or any other rigid but flexible material. In some embodiments, the lids 228 can include a locking mechanism for reversibly coupling the lids 228 to the dose containers 210 such that, for example, notches, detents, slots, and/or any other mechanism to snap-fit or latch the lids 228 to the dose containers 210. In some embodiments, the lids 228 can be simple caps that can be screwed onto threads formed on the dose containers 210. In some embodiments, the lids 228 can include a tab 230 and a depression 232 configured to serve as gripping mechanisms to assist in opening the lids. In some embodiments, the lids 228 can include slots, recesses, notches, grooves or any other gripping mechanism. In some embodiments, the lids 228 can be configured to facilitate removal of the medications from the dose containers 210. For example, the lids 228 can include an extension, for example, an arm, a strut, or any other protrusion, that protrudes into the dose container 210, such that when the lids 228 are opened, the extension lifts the dose containers 210 up and/or brings the medication up towards the user for easy removal. In some embodiments, the lids can include a protrusion that can trigger the event detection system to record an event.

In some embodiments, the lids 228 can be partially transparent, for example, to allow visual inspection of the medications inside each dose container 210, to allow lighting, and/or capture of an image by the imaging system. In some embodiments, the lids 228 can also have image capture devices mounted on them, for example, to allow "viewing" of the interior region 211 of the dose container 210 by the imaging system. In some embodiments, the lids 228 can include a unique identifier, for example, a mark, a label, a tab and/or the lids 228 can have unique shapes, which can be used to identify the dose of the day/week contained in the corresponding dose container 210. In some embodiments, the lids can also include labels for day, week, and/or dose time for each dose container (e.g., morning, noon, evening, bedtime etc.). In some embodiments, the labels can be configured to provide information on dates and on time to take a medication, and/or include multiple languages and can also provide information to the patients about the contents of the dose container 210, for example, if the dose container 210 is removed when the patient is travelling.

The base 240 of the medication storage device 200 can include a housing 242 and a base cover 244. The base cover 244 can be coupled to the housing 242, for example, via screws, rivets, snap-fit connection, heat welding, or other known methods to define an interior region. As described further below, an event detection system (not shown) and an imaging system (not shown) can be disposed in the interior region defined by the housing 242 and the base cover 244.

The base 240 (i.e., housing 242 and base cover 244) can be formed from a material that is rigid and relatively light weight, yet sturdy. Example materials include polytetrafluoroethylene, high density polyethylene, polycarbonate, other plastics, acrylic, sheet metal, any other suitable material or a combination thereof. The base 244 can be relatively smooth and free of sharp edges. The size and shape of the base 240 can be configured so that the medication storage device 200 can be disposed on a flat surface, for example, a night stand, a kitchen counter top, a study table, etc.

In some embodiments, the base cover 244 can include a plurality of apertures 246, sized and shaped to receive at least a portion of the dose containers 210. For example, when the tray 216 containing the dose containers 210 is disposed on the base 240, a portion of the dose containers 210 protrudes through the apertures 246 in the base cover 244. In some embodiments, the apertures 246 can be configured to provide an alignment mechanism for the dose containers 210 and/or to prevent lateral motion of the dose containers 210 such as, for example, when the medications are removed from the dose containers 210. In some embodiments, the apertures can also allow for "viewing" of the interior region 211 of the dose containers 210 from below. In some embodiments, the base cover 244 can also include alignment receptacles 248, configured to provide an alignment mechanism and/or a mating feature for the alignment feature 218, for example pins, on the tray 216. Said another way, the tray 216 can be reversibly coupled to the base 240 by locating and inserting the alignment features 218 of the tray 216 into the alignment receptacles 248 on the base cover 244. The alignment features 218 and the alignment receptacles 248 can be further configured such that, for example, the tray 216 can be disposed only in one orientation on the base 240.

As described herein, the base 240 of the medication storage device 200 also includes a communications module 270. The communications module 270 can be an integral part of the base 240 (e.g., coupled to the side of the housing 242 or disposed in the housing 242), removably coupleable to the base 240 and in wired or wireless communication with the medication storage device 200, or can be a separate device (e.g., Smart Phone) that is in wired or wireless communication with the medication storage device 200. In some embodiments, at least a portion of the communications module 270, for example, an audio/visual notification system can be mounted on an exterior portion of the housing 242. The communications module 270 can include speakers 272 and a display 274 (e.g., LCD, touch screen, etc.) configured to provide audible visual, and/or tactile cues, alarms, or messages to encourage patient adherence to the prescribed medication regimen.

Figure 4A:
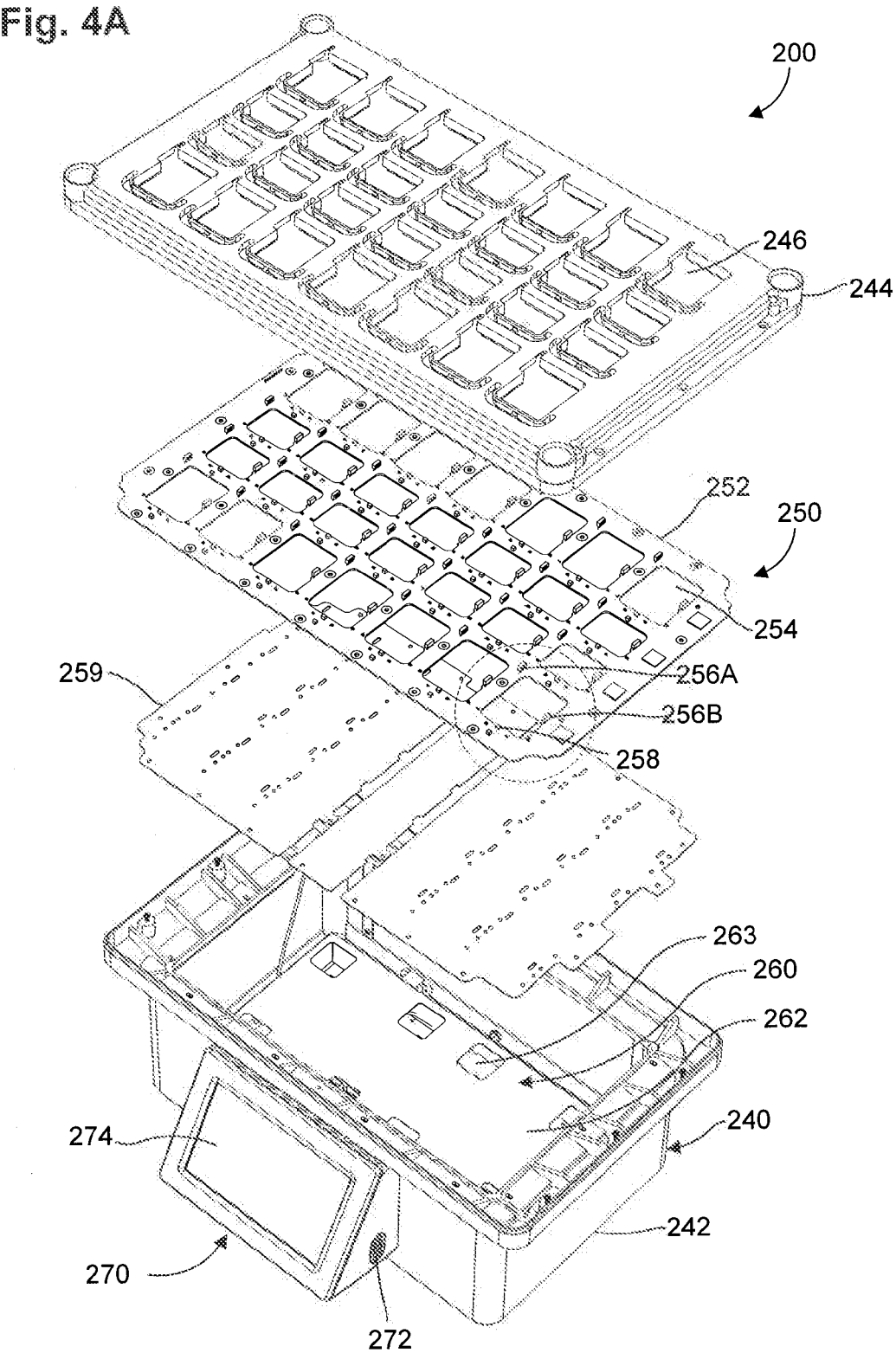
FIG. 4A is an exploded view of the event detection system included in the medication storage device of FIG. 2.
Figure 4B:
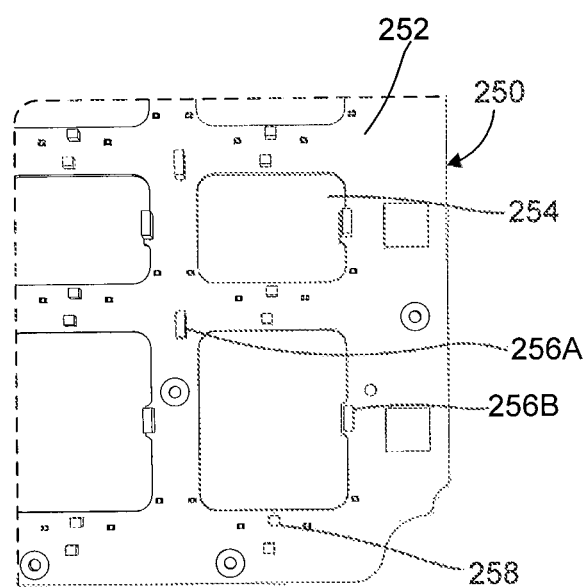
FIG. 4B is an enlarged top view of a portion of the event detection system of FIG. 4A.

Referring now to FIGS. 4A and 4B, the medication storage device 200 includes an event detection system 250 and an imaging system 260 disposed substantially within the interior region defined by the housing 242 and the base cover 244. The event detection system 250 can include a printed circuit board (PCB) 252, a plurality of sensors 256 and a lighting system 258. In some embodiments, the PCB 252 can be a standard printed circuit board made by any commonly known manufacturing process. The PCB 252 can include a plurality of openings 254, for example, to allow "viewing" of the interior region of the dose containers 210 by the imaging system 260 from below. In some embodiments, the openings 254 can be shaped and sized such that at least a portion of the dose containers 210 can protrude into the openings 254. In some embodiments, the event detection system 250 can be configured such that when the dose containers are disposed in the medication storage device, each individual dose container 210 has a first sensor 256A and a second sensor 256B (collectively referred to herein as "sensor 256") associated with it, as shown in FIG. 4B. The sensors 256 can be, for example, a position sensor, an optical sensor, a photoelectric sensor, a pressure sensor, a weight sensor or a motion sensor. In some embodiments, each of the plurality of sensors 256 can be a solid state sensor. In some embodiments, the sensors 256 can be configured to detect an event occurring in each of the plurality of dose containers 210. For example, an individual sensor or a plurality of sensors can be configured to detect dose container removal/replacement, dose container present, dose container lid opened/closed, dose container tray removal/replacement, device connected to power supply or device using backup battery. In some embodiments, the first sensor 256A can be configured to detect the opening/closing of the lids of the dose container 210. In some embodiments, the second sensor 256B can be configured to detect removal/replacement of the dose containers 210.

In some embodiments, the event detection system 250 and/or the imaging system 260 can include a lighting system 258 configured to illuminate the plurality of dose containers 210, for example, for better imaging of the dose containers 210 by the imaging system 260 and/or to view the interior region of the dose containers 210 at night or otherwise in darkness. The lighting system 258 can include, for example, a plurality of light sources such as LEDs. In some embodiments, the lighting system 258 can be further configured to perform notification functions such as, for example, illuminating the dose container 210 that correlates with the correct time (e.g., time of day and day of the week) to take a prescribed medication, blinking if a medication is not taken by the prescribed time, blinking if wrong dose container 210 is opened, and/or blinking a plurality of light sources to notify the user of a critical event. In some embodiments, a transparent member 259 can be disposed beneath the event detection system 250. The transparent member 259 can be formed from a rigid material, for example, an acrylic pane, a glass sheet, a transparent plastic sheet or any other suitable material. The transparent member 259 provides a support for the base of the dose containers 210 to rest on, and/or allows viewing of the interior region of the dose containers 210 from below, for example, by the imaging system 260.

In some embodiments, the event detection system 250 can trigger an alert that can be delivered by the communications module 270 to the user, a care giver, a family member, a pharmacy, a doctor, clinical trial manager, and/or the authorities. For example, an alert can be provided if a wrong dose container lid is opened, too many dose container lids are opened, too many dose containers removed, dose container tray removed, dose container tray replaced, device 200 battery low, and/or device 200 disconnected from power supply. In some embodiments, the event detection system 250 can be configured to trigger the imaging system 260 to capture an image of a single or a plurality of dose containers 210.

Figure 5:
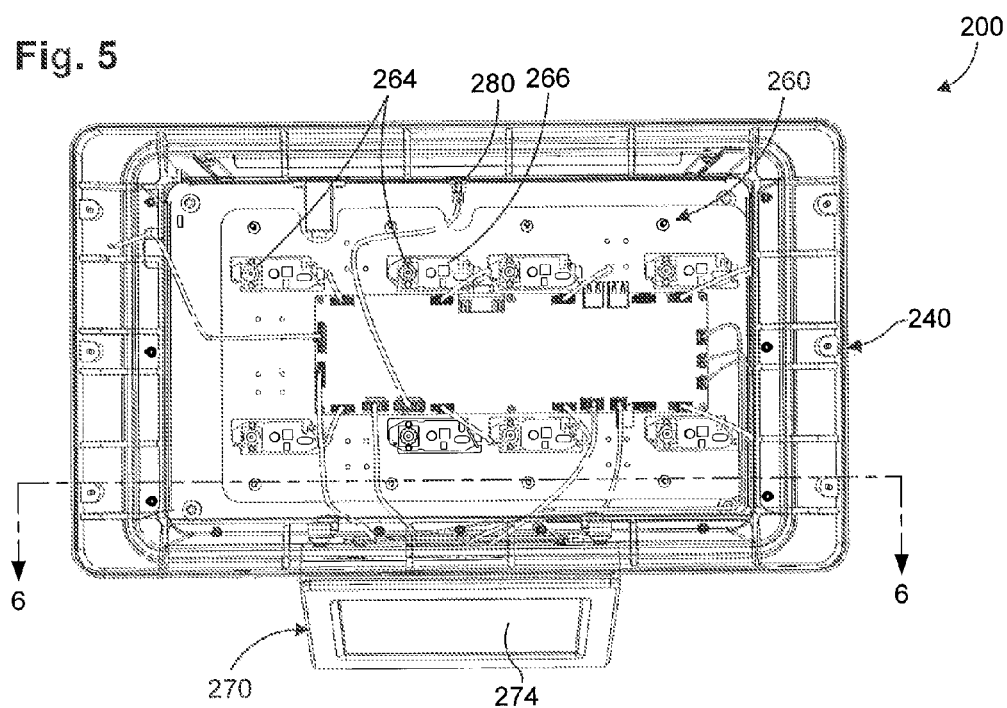
FIG. 5 is a top-view of an imaging system included in the medication storage device of FIG. 2.
Figure 6:
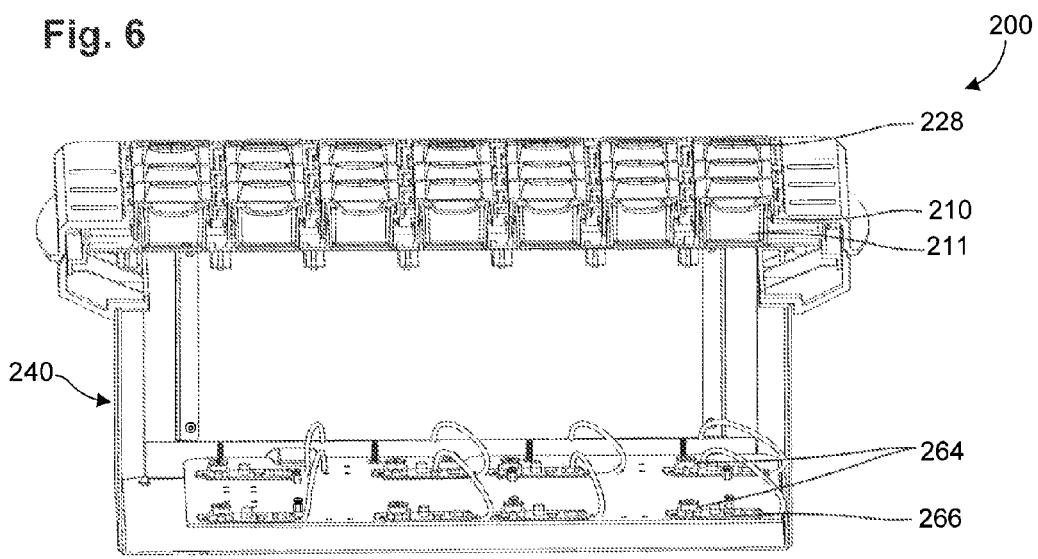
FIG. 6 is a cross-section view of the imaging system taken along the line 6-6 in FIG. 5.

Referring now also to FIGS. 5 and 6, the imaging system 260 can include a plurality of image capture devices (or cameras) 264 disposed in the housing 242 and configured to capture an image of the interior region 211 of the dose containers 210. In some embodiments, the number of cameras 264 can be equal to the number of the dose containers 210 such that, for example, each camera 264 is configured to capture images of a single dose container 210. In some embodiments, the number of cameras 264 can be substantially less than the number of dose containers 210 such that, for example, a combination of an image captured by each of the plurality of cameras 264 can show an image of the interior region 211 of all of the plurality of dose containers 210. In some embodiments, the cameras 264 can be arranged in an array. In some embodiments, the array of cameras 264 can be configured such that two or more cameras 264 in the array are capable of capturing images of any one of the dose containers 210 so failure of one camera 264 does not impact operation of the system. The "back-up" camera 264 or cameras 264 can also be used to capture images from different perspectives for use in image comparison as described herein. In some embodiments, the plurality of cameras 264 can be solid state devices, for example, CCD cameras. In some embodiments, the imaging system 260 can also include lenses, mirrors, image processing hardware/software, lighting, and/or polarizing filters. In some embodiments, the cameras 264 can include a bubble, for example a convex glass piece configured to yield images that have a partial 3D or perspective capacity, for example, the ability to look around a medication lying on edge.

In some embodiment, the imaging system 260 can be encased by a shield 262 disposed in the housing 242. The shield 262 can be formed from a metallic material, for example, a thin aluminum plate configured to serve as a Faraday cage to prevent the imaging system 260 and associated electronics from ambient electromagnetic interference. The shield 262 can include a plurality of apertures 263 such that a plurality of cameras of the imaging system (described in further detail herein) can have a clear view of the interior region 211 of the dose containers 210 from below.

In some embodiments, each of the cameras 264 can be fixedly coupled to one or more PCBs 266. The PCBs 266 can include electronics, e.g., transistors, capacitors, resistors, etc. configured to enable operation of the imaging system 260. In some embodiments, cameras 264 can also be mounted the lids 228 of the dose containers 210, for example, to allow viewing of the medications in the dose containers 210 from the top. The "top" cameras (not shown) can be coupled to the imaging system 260 via flexible electronic circuitry. The combination of top and bottom images can, for example, provide more accurate information on the status of a dose container 210. For example, the top and bottom images can provide a better opportunity to discriminate inscriptions on the medications and/or avoid small medications from being eclipsed by larger ones when viewed from only one perspective.

Figure 7:
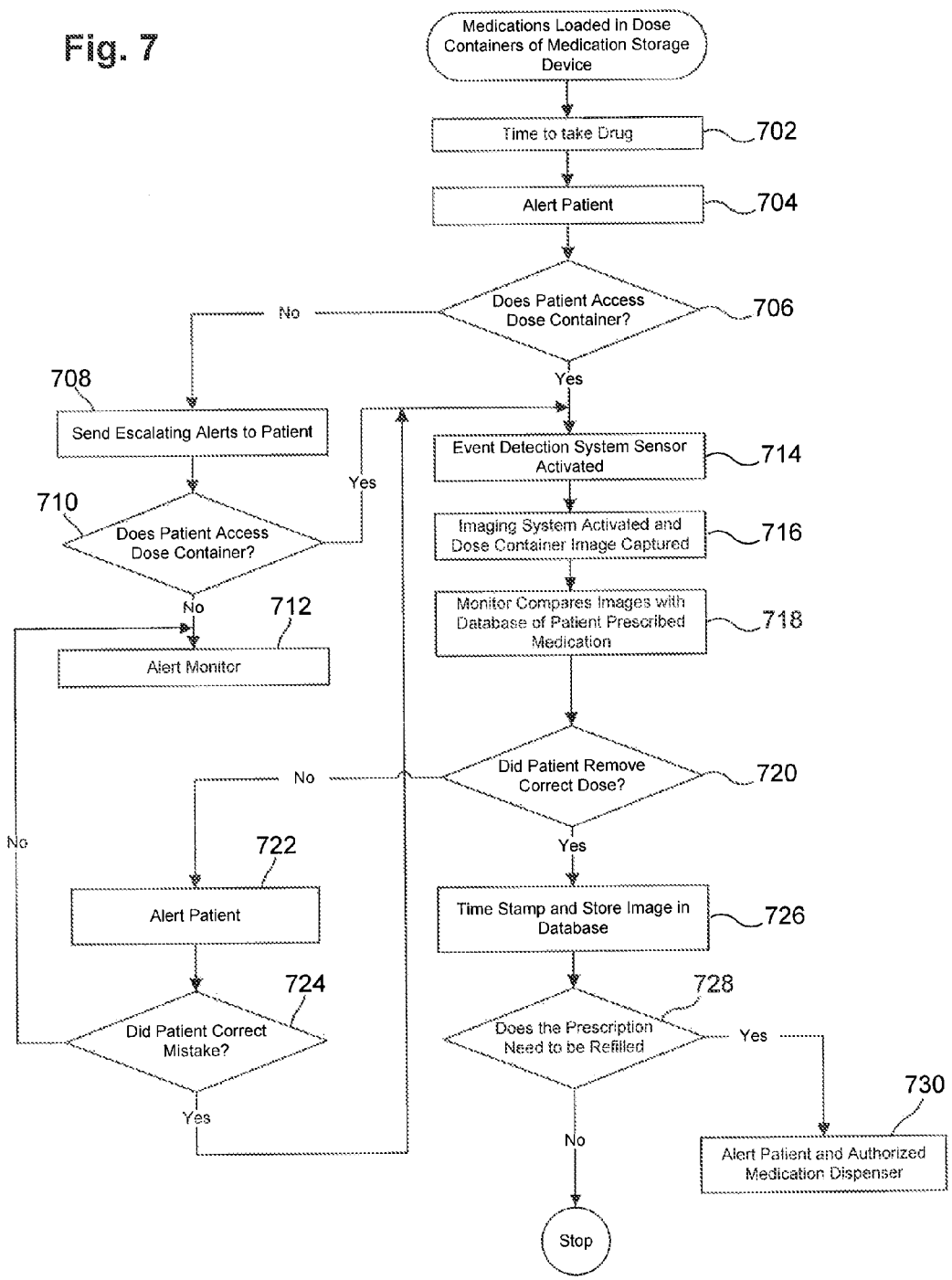
FIG. 7 illustrates a flow diagram showing a method of monitoring patient adherence to a prescribed medication regimen, according to an embodiment.

FIG. 7 illustrates a flow diagram showing an exemplary method for monitoring and ensuring patient adherence to a prescribed medication regimen using any embodiments of the medication storage device 100, 200 described herein. When it is time for a patient to take the prescribed dosage 702, the medication storage device notifies 704 the patient that it is to take the particular dosage using audio, visual and/or tactile alerts, as described herein, and the patient either accesses or fails to access the dose container 706. If the patient does not access the dose container (i.e., the event detection system does not detect access to the correct dose container), the medication storage device sends escalating alerts 708 to the patient (e.g. escalating alarm, blink LEDs, visual and/or audio message). The system/device then determines 710 if the patient accesses the dose container or not. If the patient still does not access the dose container, an alert is sent 712 to a monitor, e.g. a family member, care giver, call center, doctor, pharmacy, clinical trial manager.

If the patient accessed the appropriate dose container 706, 710, the event detection system is activated and the sensors detect an event 714 such as, for example, dose container lid opened/closed, dose container removed/replaced. The event detection system triggers and activates the image detection system 716 such that the imaging system takes an image or images of the dose container. For example, the image detection system can take an image of the dose container when the dose container lid is opened and the when the dose container lid is closed. The event and image data is communicated to the monitor and the monitor compares 718 the images to a reference image database or compares the images taken at two time points, for example, compares the image taken when lid was opened to the image taken when lid was closed. Based on the comparison, the monitor determines 720 if the patient removed the correct dosage and/or accessed the correct dose container. If the patient removed the incorrect dosage, the monitor sends an alert to the patient 722. If the patient corrects his mistake 724 (i.e., by replacing the removed medication), process repeats once a new dose container is accessed. If the patient does not correct his mistake, the monitor is alerted so that corrective action can be taken.

Once it is determined that the patient accessed the correct dose container and removed the correct dosage, the images are time stamped and stored in a database 726. If the medication storage device needs to be refilled with the prescription, then the monitor communicates this information to the patient and an authorized medication dispenser 730, e.g. pharmacy, doctor, clinical trial manager.

Figure 8:
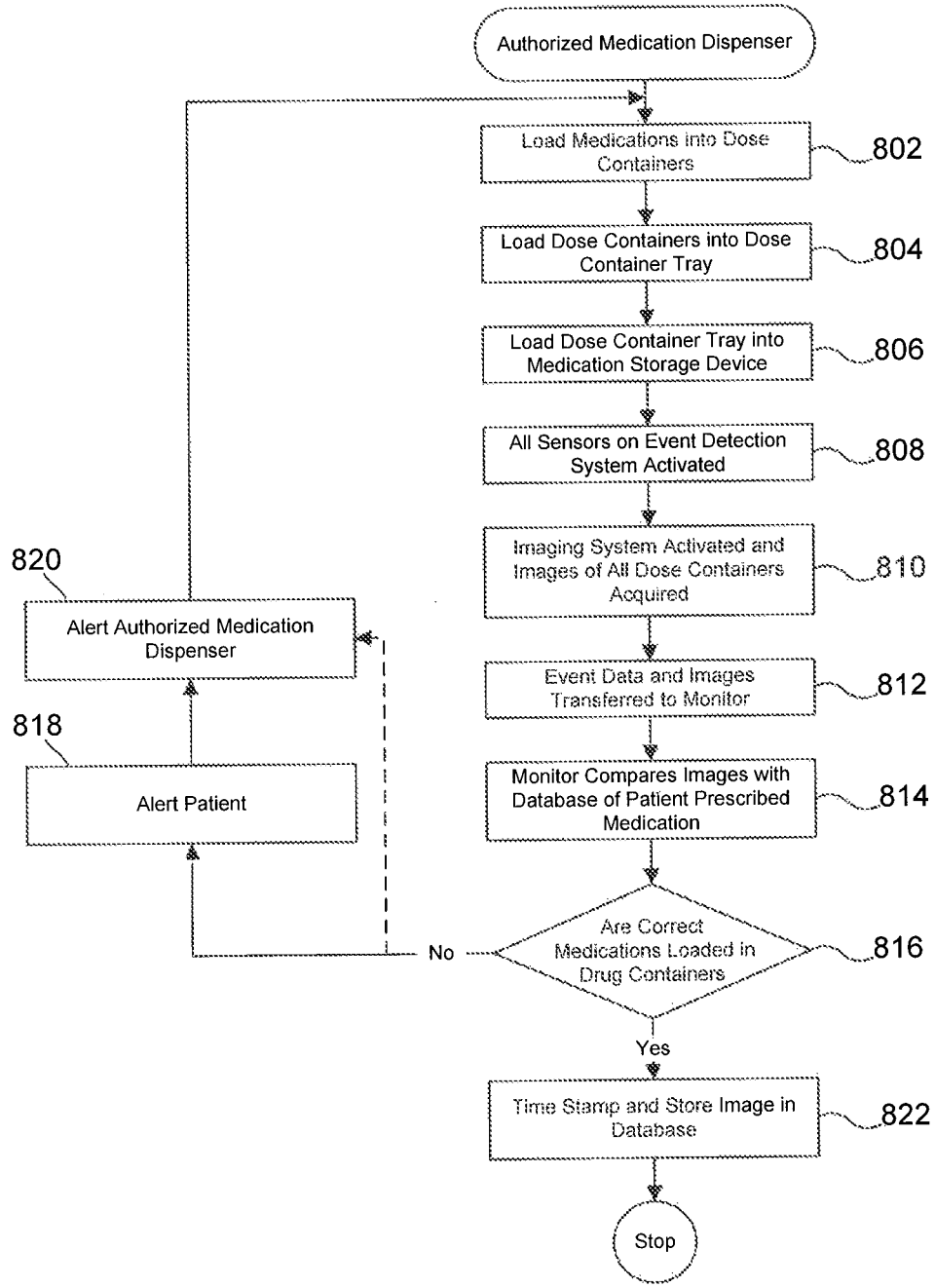
FIG. 8 illustrates a flow diagram showing a method to ensure correct medication is filled in the medication storage device by an authorized medication dispenser, according to an embodiment.

FIG. 8 illustrates a flow diagram showing an exemplary method for ensuring that the accurate prescription in the medication storage device 100, 200 described herein. An authorized medication dispenser loads a patient's prescribed medication regimen into the dose containers 802. The dose containers are loaded into the dose container trays 804. In some embodiments, the medications can be loaded into the dose containers with the dose containers already disposed in the dose container tray. The dose container tray with the dose containers disposed therein are disposed in the medication storage device 806. The loading of the containers activates all the sensors of an event detection system 808, which indicates that a dose container tray was loaded on the medication storage device. Activation of all of the plurality of sensors of the event detection system triggers all of the plurality of cameras of an imaging system such that the imaging system captures images of all of the plurality of dose containers disposed in the medication storage device 810. The event data and images are transmitted to the monitor 812 where the monitor compares the images of the dose containers with reference images of the patient prescribed medication 814 to determine if the correct medications were loaded into the dose containers 816. If a discrepancy is identified, the monitor alerts the patient of the error. For example, if there is an incorrect medication, incorrect dosage, or any of the medication that was prescribed is missing from at least one of the dose containers, the patient is notified of the error. The patient can then alert the authorized medication dispenser 820 to correct the error. In some embodiments, the monitor 816 can also directly alert the authorized medication dispenser 820. If the correct medications were loaded in the dose containers 816, the images are time stamped and stored 822.

Figure 9:
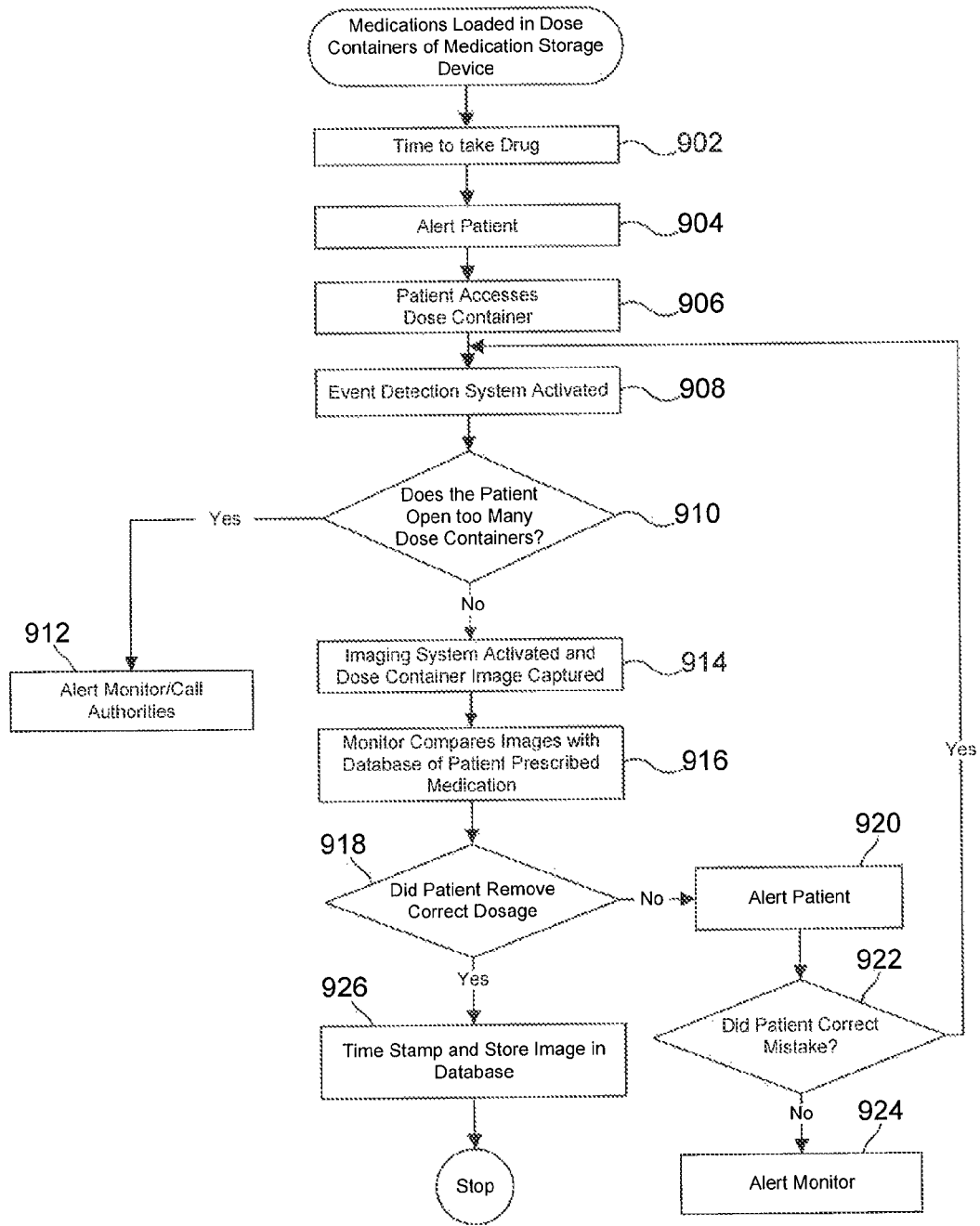
FIG. 9 illustrates flow diagram showing a method to ensure that patient does not deviate from a prescribed medication regimen, according to an embodiment.

FIG. 9 illustrates a flow diagram showing an exemplary method for ensuring that the patient does not deviate from the prescribed medication regimen using any embodiments of the medication storage device 100, 200 described herein. When it is time for the patient to take a dose for a time of the day 902, the medication storage device notifies the patient that it is time to take the particular dosage 904 using audio, visual and/or tactile notifications as described previously. The patient accesses the dose container 906, which activates the sensors of the event detection system 908 indicating an event, for example, dose container lid opened/closed and/or dose container removed replaced. If too many dose containers are opened 910 indicated by the activation of a plurality of sensors of the event detection system, the system alerts the monitor and/or calls the authorities 912. In some embodiments, the system can notify the patient, and if no corrective action is taken within a predetermined timeframe, then the system alerts the monitor and/or authorities. If the patient accessed the correct dose container only 910, then the event detection system triggers the imaging system to capture an image of the particular dose container 914. The captured images are transmitted to the monitor, wherein the monitor can compare images taken at two time points, for example, an image taken when the dose container lid was opened to an image taken when the dose container lid was closed, and/or compare captured images to reference images of the patient's prescribed medication 916. In step 918, the monitor determines if the correct dose was removed by the patient. If the monitor determines that the patient removed an incorrect dosage 918, the monitor alerts the patient. If the patient does not correct his mistake 922, the monitor is alerted 924. If the patient corrects his mistake 922 or if the patient had initially removed the correct dosage from the dose container 918, then the images are time stamped and stored 926.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combination of components, other embodiments are possible having any combination or sub-combination of any features and/or components from any of the embodiments described herein. For example, although some embodiments were described as having a prescription medication regimen that requires all dose containers in a medication storage device to be filled, it will be appreciated that any embodiment of the medication storage device can be configured to receive a prescription regimen that loads only a portion of the dose containers disposed in the medication storage device. It will be understood, that in such a scenario, the notification and alert system of the medication storage device can be configured accordingly to accommodate the new medication regimen. In addition, the specific configurations of the various components can also be varied. For example, the size and specific shape of the various components can be different than the embodiments shown, while still providing the functions as described herein.

The invention claimed is:

1. A method of monitoring a patient's adherence to a medication treatment regimen, the method comprising:
notifying the patient that it is time to take a prescribed medication;
determining if the patient has opened the correct dose container from a plurality of dose containers;
capturing a first image of the dose container when the patient opens the dose container;
capturing a second image of the dose container when the patient closes the dose container;
comparing the first image and the second image to determine which medication has been removed from the dose container;
determining whether the patient has removed the correct medication by comparing the prescribed medication to the removed medication; and
alerting the patient if an incorrect medication has been removed from the dose container.

2. The method of claim 1, further comprising:
alerting at least one a care giver, a family member, a call center, a pharmacy, and a doctor if the incorrect medication has been removed from the dose container.

3. The method of claim 1, further comprising:
alerting the patient if an incorrect dose container has been opened.

4. The method of claim 1, further comprising:
alerting at least one of a care giver, a family member, a call center, a pharmacy, and a doctor if an incorrect dose container has been opened by the patient.

5. The method of claim 1, wherein notifying the patient that it is time to take a prescribed medication includes providing a visual indication of the correct dose container to open.

6. The method of claim 1, wherein determining if the patient has opened the correct dose container from a plurality of dose containers includes monitoring each dose container in the plurality of dose containers with an event detection system.

7. The method of claim 6, wherein the event detection system includes a plurality of sensors configured to detect a change in each dose container of the plurality of dose containers.

8. The method of claim 7, wherein each of the dose containers of the plurality of dose containers has a lid and the event detection system is configured to detect a dose container lid opening.

9. The method of claim 8, wherein the first image is captured when the event detection system detects the dose container lid opening.

10. The method of claim 8, wherein the event detection system is configured to detect a dose container lid closure.

11. The method of claim 10, wherein the second image is captured when the event detection system detects the dose container lid closure.

12. A method of preventing deviations from a treatment regimen, the method comprising:
determining if a patient has opened an incorrect dose container from a plurality of dose containers;
capturing a first image of the incorrect dose container when the patient opens the incorrect dose container;
alerting the patient that the incorrect dose container from the plurality of dose containers has been opened;
capturing a second image of the incorrect dose container when the patient closes the incorrect dose container;
comparing the first image and the second image to determine if medication has been removed from the incorrect dose container;
alerting the patient if an incorrect medication has been removed.

13. The method of claim 12, further comprising:
alerting at least one a care giver, a family member, a call center, a pharmacy, and a doctor if the incorrect medication has been removed.

14. The method of claim 12, wherein determining if the patient has opened the incorrect dose container from the plurality of dose containers includes monitoring each dose container in the plurality of dose containers with an event detection system.

15. The method of claim 14, wherein the event detection system includes a plurality of sensors configured to detect a change in each dose container of the plurality of dose containers.

16. The method of claim 15, wherein each of the dose containers of the plurality of dose containers has a lid and the event detection system is configured to detect a dose container lid opening.

17. The method of claim 12, wherein comparing the first image and the second image to determine which medication has been removed from the dose container is done by an individual at a call center.

18. The method of claim 1, wherein notifying the patient that it is time to take a prescribed medication includes providing an audible indication of the correct dose container to open.

19. The method of claim 1, wherein notifying the patient that it is time to take a prescribed medication includes providing a tactile indication of the correct dose container to open.

20. The method of claim 1, wherein comparing the first image and the second image to determine which medication has been removed from the dose container is done by an individual at a call center.

* * * * *